United States Patent [19]

Peters et al.

[11] Patent Number: 4,951,860
[45] Date of Patent: Aug. 28, 1990

[54] METHOD AND APPARATUS FOR STORING, DISPENSING AND APPLYING SURGICAL STAPLES

[75] Inventors: Ronald L. Peters; Rudolph Peters; William Taylor, all of Danville, Calif.

[73] Assignee: Edward Weck & Co., Research Triangle Park, N.C.

[21] Appl. No.: 138,145

[22] Filed: Dec. 28, 1987

[51] Int. Cl.⁵ ............................................. A61B 17/00
[52] U.S. Cl. ........................................ 227/177; 227/19; 227/82; 227/121
[58] Field of Search ............... 227/DIG. 1, 67, 19, 227/82, 121, 175, 176, 177

[56] References Cited

U.S. PATENT DOCUMENTS

| | | | |
|---|---|---|---|
| 2,228,778 | 1/1941 | Pankonin | 227/121 |
| 2,733,441 | 2/1956 | White | 72/410 |
| 3,650,453 | 3/1972 | Smith, Jr. | 227/19 |
| 3,954,108 | 5/1976 | Davis | 128/325 |
| 3,955,581 | 5/1976 | Spasiano et al. | 128/334 |
| 4,043,504 | 8/1977 | Hueil et al. | 227/19 |
| 4,049,177 | 9/1977 | Bussard | 227/67 |
| 4,077,557 | 3/1978 | Green | 227/121 X |
| 4,125,215 | 11/1978 | Jenkins | 227/67 |
| 4,391,402 | 7/1983 | Campbell et al. | 227/121 |
| 4,410,125 | 10/1983 | Noiles et al. | 227/19 |
| 4,470,532 | 9/1984 | Froehlich | 227/19 |
| 4,478,362 | 10/1984 | Foslien | 227/19 |
| 4,576,166 | 3/1986 | Montgomery et al. | 227/DIG. 1 |
| 4,592,498 | 6/1986 | Braun et al. | 227/DIG. 1 |
| 4,598,711 | 7/1986 | Deniego | 227/DIG. 1 |

FOREIGN PATENT DOCUMENTS

EP0040157  11/1981  European Pat. Off. .
WO80/00230 2/1980  PCT Int'l Appl. .

OTHER PUBLICATIONS

Skin & Fascia, Model SFM-SP-1984.

Primary Examiner—Paul A. Bell
Attorney, Agent, or Firm—Harris Zimmerman

[57] ABSTRACT

A method and apparatus for storing, dispensing, and applying surgical staples includes a pistol-like tool having a handle portion with a manually movable trigger lever, and a rotatable barrel portion with a staple track for storing staples in parallel, stacked, column fashion, the axis of the column extending generally colinearly with the barrel axis. The staples are urged distally in the track, and the distal track portion is curved out of axial alignment so that the distal staples are urged into points-first alignment. A form tool is slidably disposed in the barrel portion and adapted to advance and urge the distal-most staple against an anvil tool to crimp the staple. The form tool includes a drag spring which engages the distal-most staple in the staple track as the form tool retracts after a crimping cycle, pulling the distal-most staple from the track into a dispensing position for the next dispensing cycle. A drive block connected to the form tool and the trigger lever is mounted in the apparatus for reciprocal translation along a coaxial drive track. The drive block includes a pawl engaging ratchet teeth in the drive track, so that the block is urged distally by trigger actuation and proximal translation is prevented. The pawl includes a release slide actuated by translation of the block to the distal end of the drive track, coincident with full distal translation of the form tool and crimping of the dispensed staple, the release slide disengaging the pawl and allowing the drive block to return proximally.

34 Claims, 8 Drawing Sheets

FIG_3

FIG_9

FIG_7

FIG_6

FIG_8

FIG_10

FIG_11

FIG_15

FIG_20

FIG_12

FIG_13

FIG_14

FIG_16

METHOD AND APPARATUS FOR STORING, DISPENSING AND APPLYING SURGICAL STAPLES

BACKGROUND OF THE INVENTION

In recent years various forms of surgical stapling tools have been introduced to surgeons and others in the medical treatment community. Experience with these tools has shown that although stapling tools are often a great improvement over prior suturing techniques, the tools have exhibited shortcomings that should be addressed in newer tool designs.

For example, many surgeons have found that in using a stapling tool it is preferable to partially dispense and crimp a staple, so that the staple extends from the tool and the placement of the staple points can be visualized easily. This action requires that the tool is capable of partially forming the staple and retaining the staple in that disposition. Unfortunately, some surgical stapling tools cannot perform this function, due to the fact that a partially formed staple is held too loosely in the tool jaws to permit effective placement of the staple in the partially formed configuration. In other tools, interruption of a dispensing cycle can cause the tool to initiate a new dispensing cycle, resulting in jamming of the mechanism.

Also, surgeons demand a tool that is jam-proof and trustworthy; obviously, a tool that fails during surgery creates delays and frustrations that are aggravating, costly, potentially dangerous, and completely unacceptable. Many prior art surgical stapling tools have complex mechanisms involving many components, close tolerances, and critical engagements. Factors such as thermal dimensional changes, casual impact to the tool, or erratic manufacturing techniques can cause prior art tools to jam and fail.

A further criticism of prior art tools involves their "feel" and ease of use. The feel of the tool is an intangible quality that involves such factors as the ability to visualize the staple placement, the mechanical advantage of the tool mechanism, the relationship between manual movement and progress in the staple dispensing cycle, the smoothness of actuation of the mechanism, and the like. Also, some mechanisms require a "precocking" motion, before each dispensing cycle, than can introduce an awkward manipulation into the use of the tool.

SUMMARY OF THE PRESENT INVENTION

The present invention generally comprises a method and apparatus for storing, dispensing, and applying surgical staples. The apparatus includes a pistol-like tool having a handle portion with a manually movable trigger lever, and a rotating barrel portion with a staple track for storing staples in parallel, stacked, column fashion, the axis of the column extending generally colinearly with the barrel axis. Thusl the barrel also serves as the cartridge for holding the staples. The staples are urged distally in the track by spring means, and the distal track portion is curved out of axial alignment so that the distal staples are gradually urged into points-first alignment as they traverse the curved portion. A form tool is slidably disposed in the barrel portion and adapted to advance past the distal end of the staple track and urge the distal-most staple against a fixed anvil tool to crimp the staple. The form tool includes a drag spring which engages the distal-most staple in the staple track as the form tool retracts after a crimping cycle, pulling the distal-most staple from the track into a dispensing position for the next dispensing cycle.

The tool includes a drive track oriented parallel to the barrel axis and located within the proximal end of the barrel, and a drive block connected to the form tool and the trigger lever and mounted for reciprocal translation along the drive track as the trigger is actuated. The drive block includes a pawl engaging ratchet teeth formed in the drive track and oriented to prevent proximal translation of the block and the form tool. The trigger is pivotally mounted in the handle, and the inner end of the trigger includes gear teeth that engage like-formed teeth in the drive block in rack-and-pinion fashion. The pawl includes a release slide actuated by translation of the block to the distal end of the drive track, coincident with full distal translation of the form tool and crimping of the dispensed staple, the release slide disengaging the pawl and allowing the drive block to be returned proximally by resilient means. The rack and pinion drive engagement of the block and form tool, together with the ratchet teeth engagement, permit the dispensing cycle to be interrupted at any degree of trigger actuation with the dispensed staple firmly retained in its position.

The tool also includes a cqunter assembly, disposed within the proximal end of the barrel portion, for indicating the number of surgical staples remaining to be dispensed from the tool. The counter assembly includes a pair of concentric, nested wheels having indicia formed about the outer surface thereof and ratchet teeth formed on the outer edges thereof. A counter pawl extends from one surface of the drive block to engage the counter ratchet teeth at the proximal end of each reciprocation of the drive block. One wheel bears units indicia, and the other bears tens indicia, and the appropriate indicia are visualized through a counter window in the proximal barrel portion.

DESCRIPTION OF THE PREFERRED EMBODIMENT

Figure 1:
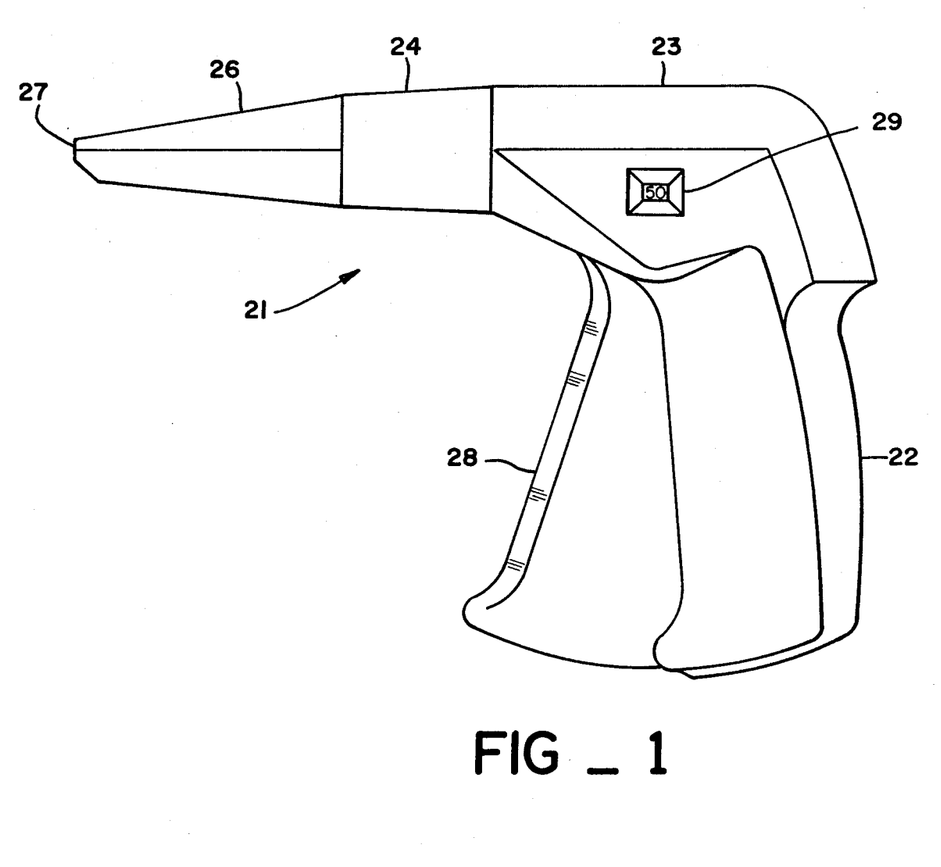
FIG. 1 is a side elevation of the tool of the present invention for storing, dispensing, and applying surgical staples.
Figure 2:
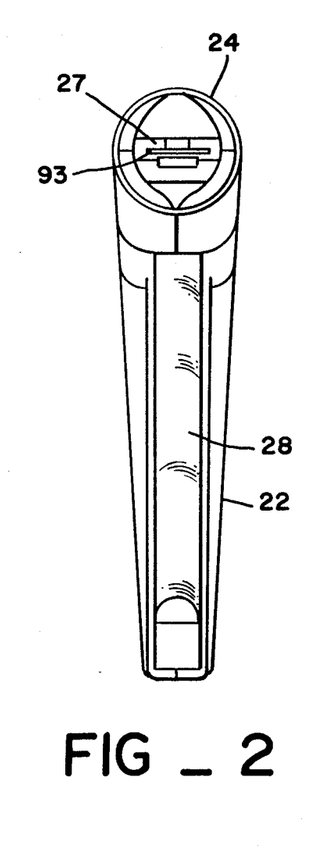
FIG. 2 is a front end elevation of the tool shown in FIG. 1.

The present invention generally comprises a method and apparatus for storing, dispensing, and applying surgical staples for suturing wounds, incisions, and the like. With regard to FIGS. 1 and 2, the apparatus comprises a tool 21 having a pistol-like configuration, with a handle portion 22 and a barrel comprising a proximal barrel portion 23, a medial barrel portion 24, and a distal barrel portion 26. The surgical staples are stored within the barrel portion 26, and dispensed and crimped at the distal end 27 thereof, as will be explained in detail in the following description. A trigger lever 28 is pivotally mounted in the portion 23 and disposed to be squeezed by manual action in proximation to the handle 22 to actuate the dispensing mechanism of the tool.

Figure 3:
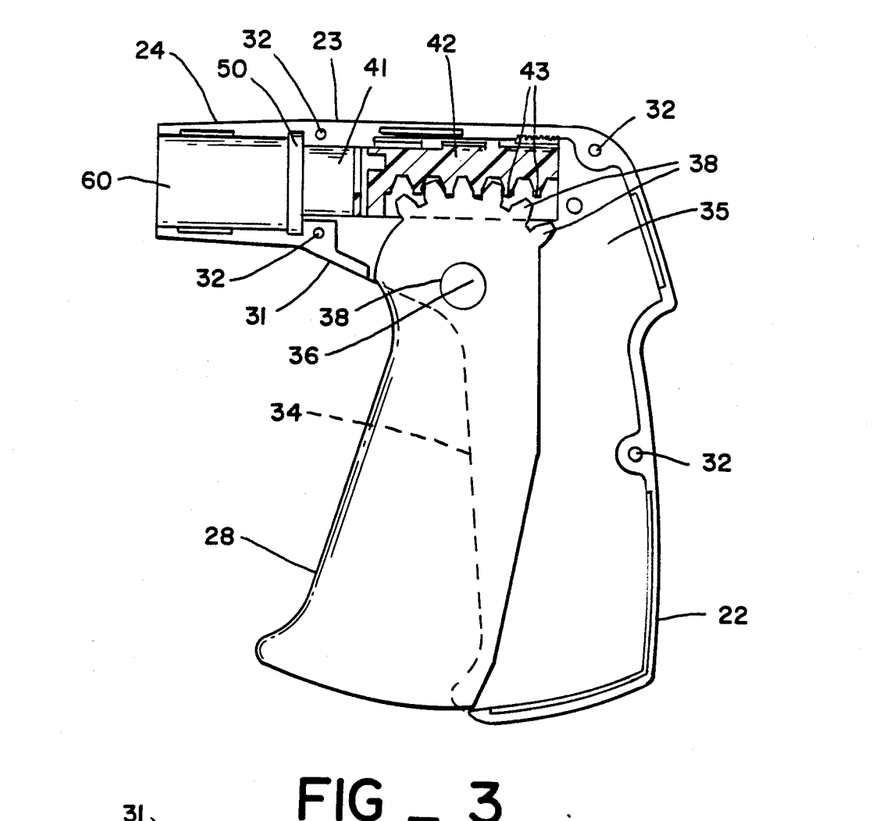
FIG. 3 is a side elevation of one housing portion of the handle and proximal barrel portion of the tool of the present invention.
Figure 4:
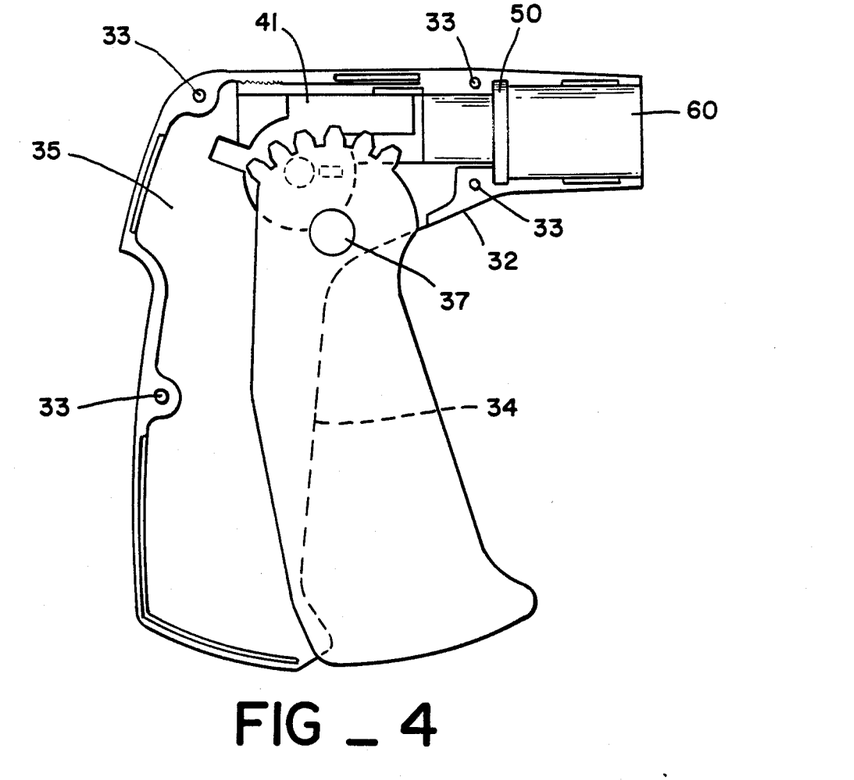
FIG. 4 is a side elevation of the other housing portion of the handle and proximal barrel portion of the tool of the present invention.

With regard to FIGS. 3 and 4, the portions 22, 23, and 24 of the tool 21 are formed by a pair of housing members 31 and 32. The housing members are preferably molded of durable plastic material, and are formed with side walls having generally identical conformations for mating engagement therebetween. The side wall of housing member 31 includes a plurality of pins 32 extending therefrom to engage corresponding holes 33 formed in the side wall of the housing member 32 to join the housing members in precise alignment. The side walls also define cavities 35 in each housing member which are combined in the assembled housing members to define an enclosed space which supports and protects the mechanism described below. The side walls together further define a slot opening 34 through which the trigger lever 28 extends from the handle portion.

A post 36 extends from the interior surface of the cavity of the housing member 32, and is received in a recess 37 formed in registration therewith in the surface of the cavity 35 of the housing member 33. The inner end portion of the trigger lever 28 is provided with a hole 38 through which the pin extends to secure the trigger lever in pivoting fashion. The inner end surface of the trigger lever is provided with a plurality of pinion gear teeth 38 arrayed about a radius generally concentric with the pin 36. Confronting interior surface portions 41 of the cavities 35 are recessed to define a linear drive channel or track 41 extending generally coaxially with the barrel portions 24 and 26. A drive block 42 is received and retained within the drive track 41 in freely translating fashion.

The drive block 42 is a critical component of the present invention, in that it converts the rotary motion of the trigger lever 28 to linear translating motion to actuate the dispensing and crimping mechanism of the tool, as described below. The drive block 42 is provided with a plurality of rack teeth 43 formed in confronting engagement to the pinion teeth 38 of the trigger lever, so that the drive block is driven reciprocally in the drive track 41 by squeezing and releasing the trigger lever. Furthermore, this drive engagement provides a constant mechanical advantage, and permits virtually no free play in the mechanism.

With regard to FIGS. 6, 7, 9 and 10, the drive track is further provided with a plurality of ratchet teeth 46 arrayed in linear fashion along a portion thereof and directed toward the distal end of the tool barrel. The drive block is provided with a drive pawl 47 having several rows of ratchet teeth 48 formed in complementary fashion to the teeth 46 and disposed to engage the teeth 46 to prevent proximal translation of the drive block while permitting distal translation of the drive block. The pawl 47 is mounted on a pivot pin 49 on the drive block, and a spring 51 secured to the drive block biases the pawl into engagement with the ratchet teeth 46. The ratchet teeth 46 and 48 are of extremely fine pitch, so that proximal free play motion of the drive block is substantially eliminated.

The drive block further includes a channel 52 formed in the upper surface thereof and extending generally colinearly with the barrel axis. The channel is disposed directly adjacent to the pawl 47 and the pivot pin 49. A slide member 53 is received in the channel 52 in freely translating fashion, and is provided with a ramped, camming surface 55 at the proximal end thereof that is disposed to impinge on the pawl 47 as the slide member translates proximally with respect to the drive block. The slide member further includes a pair of tabs 54 extending laterally from the distal end thereof. The drive track 41 includes a foreshortened auxiliary track 56 in which the tabs 54 translate as the drive block is translated by the trigger actuation. The track 56 is dimensioned in the axial direction so that as the drive block is translated to approach the desired limit of distal travel, the tabs 54 strike the end of the track 56 and stop the slide member, causing the slide member to translate proximally with respect to the advancing drive block. The proximal camming surface 55 impinges on the pawl 47, pivoting the pawl about the pin 49 and disengaging the ratchet teeth 46 and 48. The drive block is thus freed for retrograde motion in the proximal direction when the trigger lever is released. As the drive block translates proximally to the end of the drive track 41, the proximal end of the auxiliary track is engaged by the tabs 54, causing the slide member to translate distally with respect to the drive block and return to its initial distal disposition for the next dispensing cycle. The pawl is thus released by the slide member, and is urged by spring 51 to re-engage the ratchet teeth 46.

Figure 16:
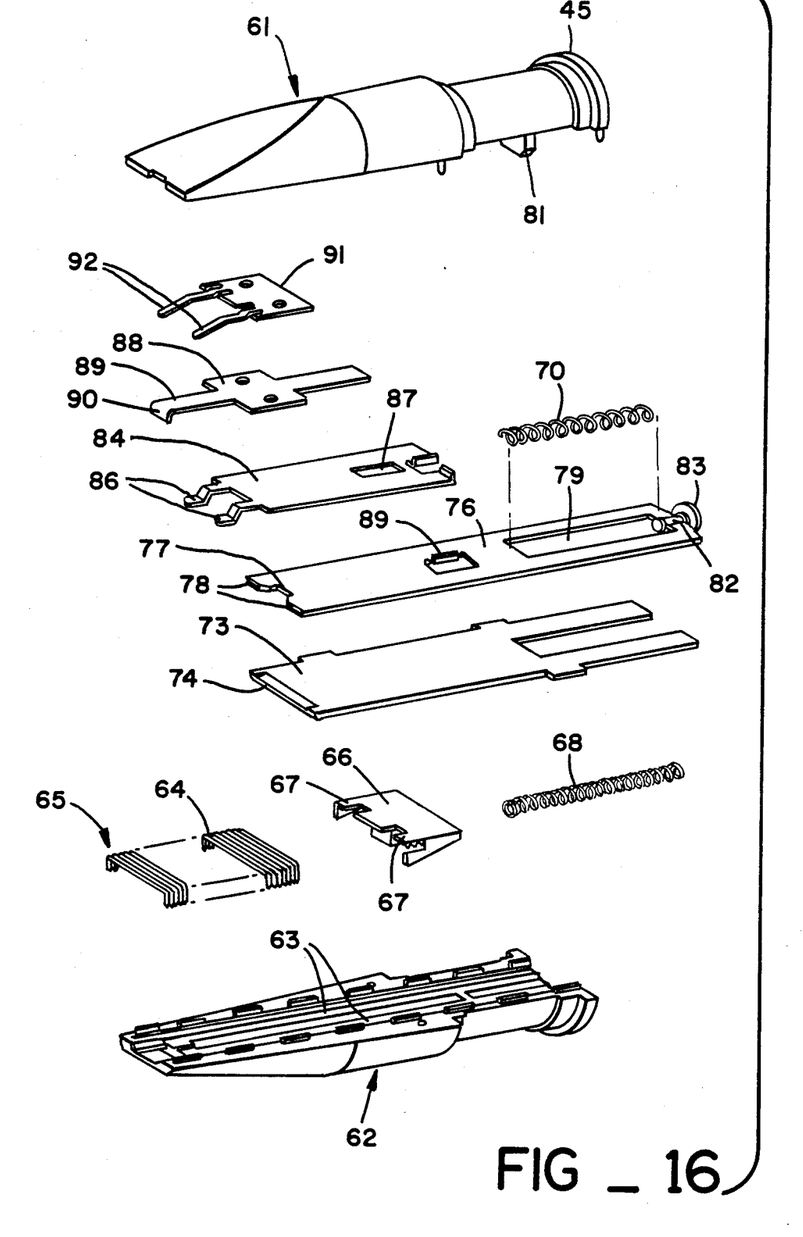
FIG. 16 is an exploded view of the rotatable barrel assembly of the tool of the present invention.

The medial and distal barrel portions of the tool of the present invention are defined by a pair of axially extending barrel housing members 61 and 62, shown in FIG. 16. The housing members 61 and 62 define the distally tapered outer configuration of the barrel, and are provided with confronting side walls disposed for complementary fit to form a smoothly contoured outer assembly. The members 61 and 62, which are preferably molded of durable plastic material, are provided with semi-cylindrical proximal end portions which together define a cylinder dimensioned to be received within the bore 60 defined by the housing members 31 and 32 (FIGS. 3 and 4. An annular flange 45 extending radially outwardly from the proximal end of the assembled housings 61 and 62 is dimensioned to be received within an annular groove 50 at the inner (proximal) end of the bore 60 with sufficient clearance to permit free rotation of the barrel portion about the barrel axis, yet retain the barrel assembly to the assembled housings 31 and 32.

The barrel assembly also includes interior features and surfaces which are integral components of the staple storing, dispensing, and crimping mechanism of the tool. For example, a pair of axially extending, laterally spaced slots 63 are formed in the interior of housing member 62 to comprise a staple track for storing a large plurality of surgical staples 64. The staples are stored in a parallel, stacked column 65, with the webs and legs of adjacent staples impinging in parallel relationship to provide the most volumetrically efficient staple storage. A staple pusher 66 is translatably received in the staple track, and is provided with a pair of pusher tabs 67 which impinge on the proximal-most staple in the track. A compression spring 68 is also received in the housing 62 to resiliently urge the staple pusher distally and apply constant force to the staple column.

It should be noted that the staples 64 in the column 65 are not adhered nor joined to each other, but are maintained in their column configuration by the compressive force of the pusher 66. With regard to FIGS. 17-19, a salient feature of the invention is that the distal end of the staple track is provided with a non-linear portion 71 curved out of the plane defined by the webs of the staple column in the linear track portion, so that the staple legs fan out as the staples traverse the track portion 71. Indeed, the staples are gradually rotated in track portion 71 from their column orientation, in which the staple legs are transverse to the barrel axis, to a points-first orientation in which the staple legs are parallel to the barrel axis. It should be noted that the pusher tabs 67 of the staple pusher 66 are provided with serrated portions 72 so that the tabs 67 may be sufficiently flexible to traverse the curved track portion 71. Thus the staple pusher is capable of delivering all the staples in the storage track to the dispensing and crimping portion of the tool. Even the proximal-most staple in the track is held in position by the tabs 67 prior to its engagement by the drag spring, as described below.

Also secured within the barrel housing assembly 61-62 is a track cover panel 73 which secures the staples 64 and pusher 66 in the staple track. The distal edge 74 of the cover panel 73 is rounded to accommodated the curved track portion 71. The housing members 61 and 62 also define a channel in which a form tool 76 is disposed for translation parallel to the axis of the barrel. The form tool comprises an elongated, planar web having a notch 77 formed in the distal end thereof to define a pair of staple-engaging lands 78. The lands 78 are spaced to engage laterally opposed end portions of a staple web, and are further provided with a pair of laterally extending grooves formed in the respective end surfaces thereof to engage the staple web. The proximal portion of the form tool is provided with a rectangular hole 79 extending therethrough and disposed to receive a guide post 81 extending from the housing 61. The post 81 acts as a stop to limit the proximal and distal translation of the form tool, as well as to mount a compression spring 70 disposed between the post 81 and the proximal end of the slot.

Figure 7:
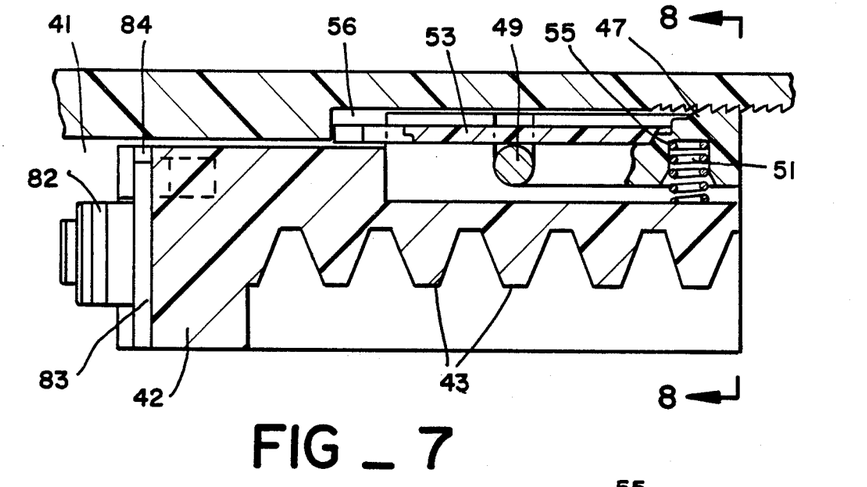
FIG. 7 is an enlarged, fully cross-sectional view of the drive block mechanism of the present invention, shown in its proximal position.
Figure 9:
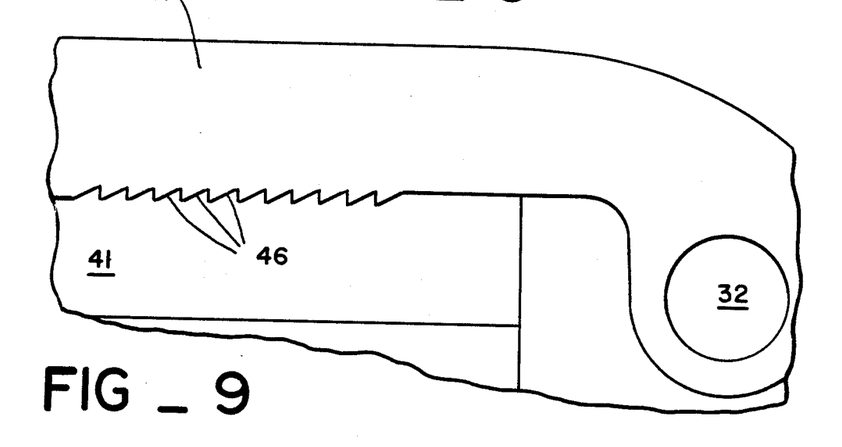
FIG. 9 is an enlarged, cutaway view of the drive block track and ratchet teeth of the present invention.
Figure 10:
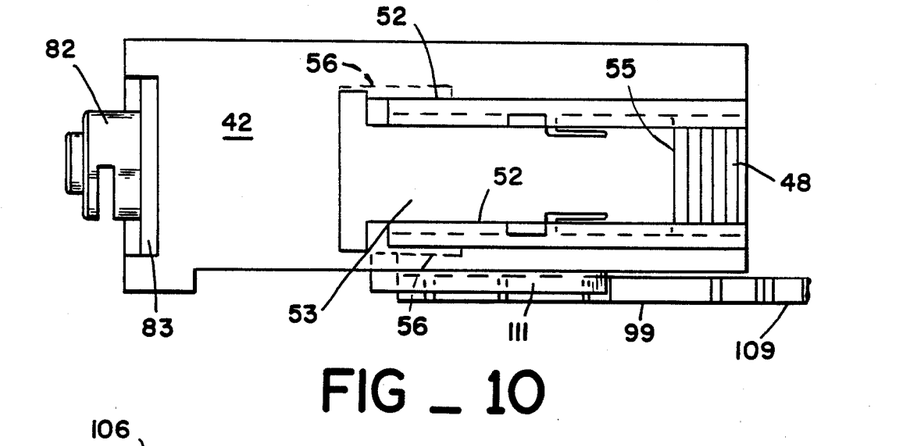
FIG. 10 is a plan view of the drive block mechanism and its engagement with the counter assembly of the tool of the present invention.

The proximal end of the form tool is also provided with a coupling member 82 secured thereto. The coupling member includes a disk 83 dimensioned to be received within a slot 84 provided in the distal end of the drive block 42, as shown in FIGS. 7 and 10. The disk is freely rotatable in the slot 84, so that the barrel assembly may be rotated about the barrel axis while the form tool remains mechanically connected to the drive block. It may be appreciated that reciprocal translation of the drive block caused by trigger actuation and release results in like reciprocal motion of the form tool.

Another component of the dispensing and crimping mechanism is a finger spring 84, which comprises a planar web member resting on one surface of the distal end portion of the form tool and disposed to translate axially in the barrel and independently of the form tool. The finger spring includes a pair of resilient fingers 86 extending distally therefrom and spaced laterally approximately the same amount as the lands 78. The web portion of the finger spring is provided with a rectangular hole 87, and a lug 89 extends from the form tool through the hole 87 to link the translational motion of the two components together, as will be explained below. When the form tool is in the retracted (proximal) position, shown in FIG. 19, the fingers 86 extend slightly distally of the lands 78 to define a gap 80 therebetween dimensioned to receive and retain the web of a staple 64.

The crimping mechanism also includes an anvil member 88 secured fixedly to the distal interior surface of the barrel housing 61. The anvil member includes a shank 89 extending axially and distally therefrom and terminating in an anvil 90 extending transverse to the barrel axis. An ejector spring 91 is secured fixedly between the anvil member and the interior of the barrel housing 61, and included a pair of resilient arms 92 extending distally therefrom. The arms 92 are spaced apart laterally to straddle the anvil and shank, and are spaced slightly inwardly of the fingers 86.

Figure 18:
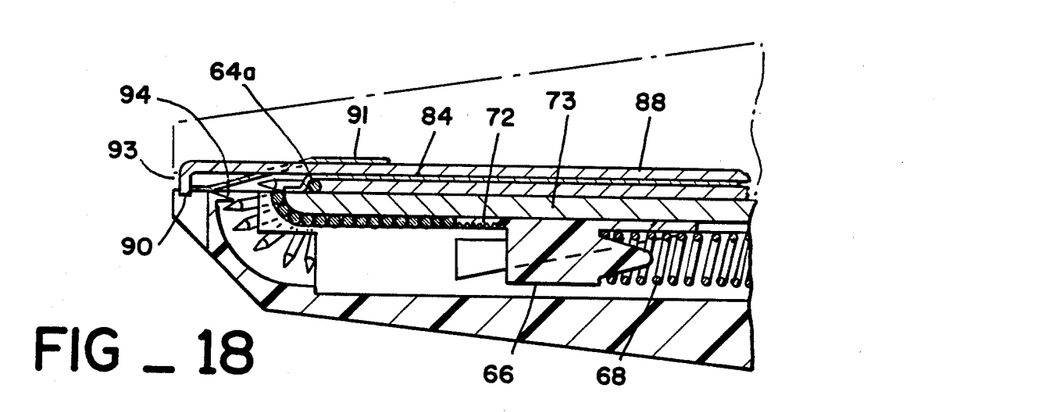
Figure 19:
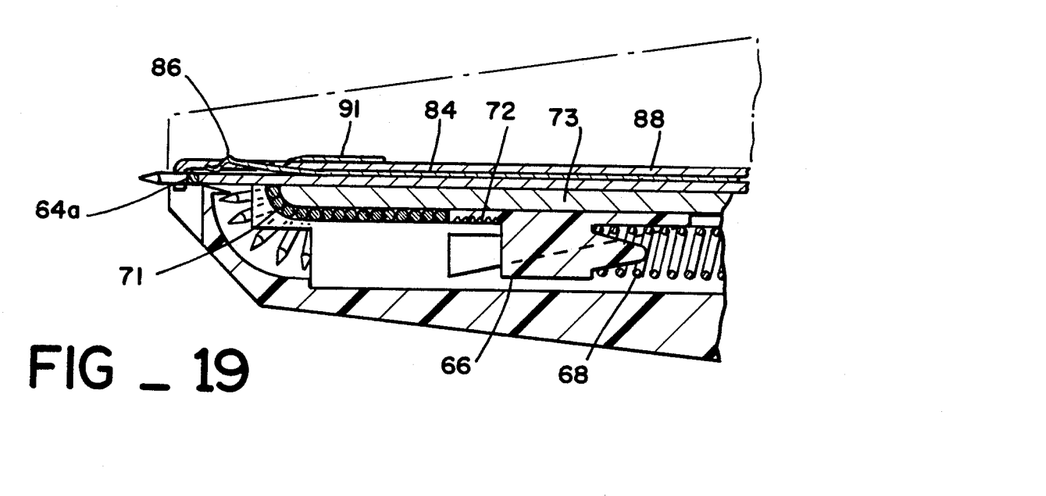

At the distal end of the barrel housing assembly, a slot formed therebetween defines a linear feed path 93 in which the staples 64 are serially dispensed, crimped, and ejected from the tool. It may be noted, with regard to FIGS. 17-19, that the anvil projects into the feed path 93, and the fingers 86 and the ejector arms 92 also project into the feed path 93. In the initial quiescent position, shown in FIG. 18, the form tool 76 and the finger spring 84 are retracted to their proximal position, and the web of a staple 64a is retained therebetween. As the trigger lever 28 is squeezed and the drive block 42 translates distally, the form tool is likewise translated distally. The lands 78 of the form tool impinge on laterally spaced portions of the web of the staple 64a, pushing the staple 64a past the fingers 86 and toward the anvil 90. The fingers 86 bend resiliently to release the staple 64a, as shown in FIG. 19. The web of staple 64a then encounters the arms 92 of the ejector spring, which impinge on the staple web and frictionally resist any further distal translation thereof.

As the form tool advances farther distally, the advancing staple and the form tool itself urge the ejector arms to bend resiliently out of the feed path. The medial portion of the web of staple 64a impinges on the anvil 90, while the laterally opposed portions of the staple web are driven past the anvil by the lands 78 of the form tool, as in FIG. 19. It should be noted that the notch 77 of the form tool is dimensioned to receive the anvil 90 therein. The lands 78 thus cause the staple web to bend about the anvil to an angle of approximately 90°, bringing the points of the staple legs into confronting, spaced apart opposition. The staple 64a thus becomes crimped, securing together the tissue into which it is directed as the process described above takes place.

It should be noted that the dispensing and crimping process can be interrupted at any point by the user of the tool, merely by halting manual squeezing of the trigger lever 28. The form tool cannot retract proximally, due to the action of the ratchet teeth 46 and 48, and the staple 64a is initially retained between the lands 78 and the frictional engagement of the ejector arms 92. After the ejector arms are driven out of the feed path by the advancing staple, the staple web is pinched between the anvil and the lands, and is likewise firmly retained in position if the crimping process is halted. Thus the present invention facilitates a preferred method of surgical staple application, in which the staple legs are extended from the distal tip of the barrel and partially crimped, after which the points of the staple are carefully placed in the tissue and the crimping process is completed.

The components of the tool are dimensioned and arranged so that just prior to full distal translation of the form tool 76 and crimping of the staple 64a there is actuation of the slide 53 and release of the pawl 47. Release of the trigger lever causes resilient force to be applied by spring 70, which is compressed during proximal advance of the form tool, so that spring 70 urges the form tool to retract proximally. As the form tool retracts, the ejector arms 92 are freed to return to their quiescent position in the feed path 93, as in FIG. 17. The ejector arms thus urge the web of staple 64a to slide out of engagement with the anvil 90, releasing the crimped staple from the tool. Thus staple release is accomplished without any manipulation of the tool, other than release of the trigger lever.

Figure 17:
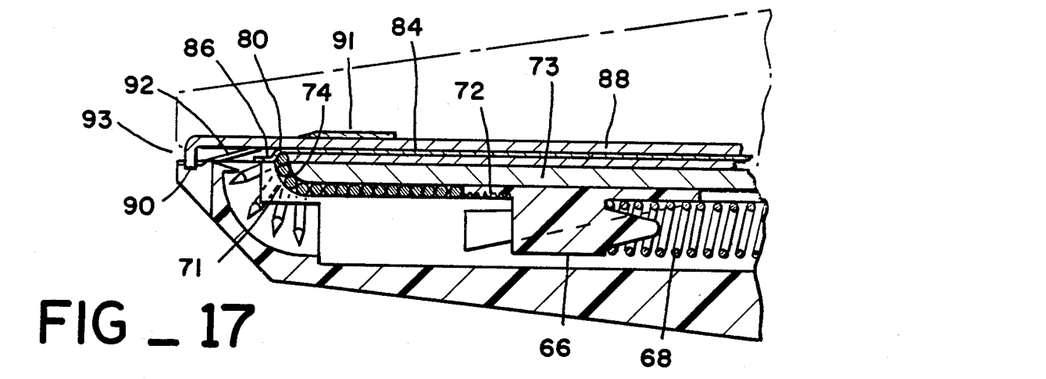
FIGS. 17–19 are a sequence of cross-sectional views of the rotatable barrel assembly, showing the actuation of the form tool and advancement and dispensing of a surgical staple.

After further retraction of the form tool, the distal end of the form tool clears the fingers 86 and permits the fingers to re-assume their quiescent position in the feed path 93. The engagement of lug 89 in hole 87 defines a gap 80 between the fingers 86 and the lands 78, the gap 80 being dimensioned to receive the web of the next staple to be dispensed. As the form tool and the fingers retract proximally together past the outlet of the curved staple track portion 71, the resilient pressure of the staple pusher 66 causes the web of the distal-most staple in the curved track portion to slide into the gap 80 between the fingers and the lands, as shown in FIG. 17. Further proximal translation of the form tool and finger spring pulls the captured staple from the staple storage track and places it in the feed path 93, as shown in FIG. 18. The dispensing mechanism is thus reloaded for the next dispensing cycle.

It should be noted that the staple track portion 71 includes a lip 94 past which the points of the staple are translated as the staple web is captured and pulled from the track portion 71. After the staple points clear the lip and the staple enters the feed path 93, the legs of the captured staple cannot return past the lip because the next distal staple impinges on the legs of the captured staple, as shown in FIG. 18. Thus the captured staple is directed only along the feed path.

Figure 5:
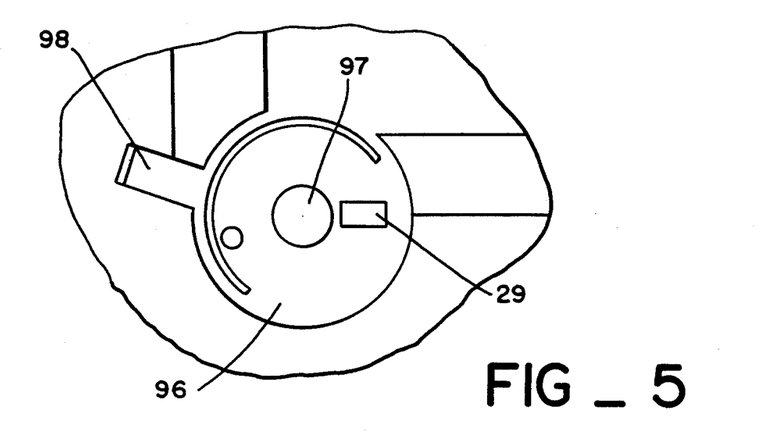
FIG. 5 is an enlarged, detailed view of the counter assembly placement within the housing portion shown in FIG. 4.
Figures 6, 8:
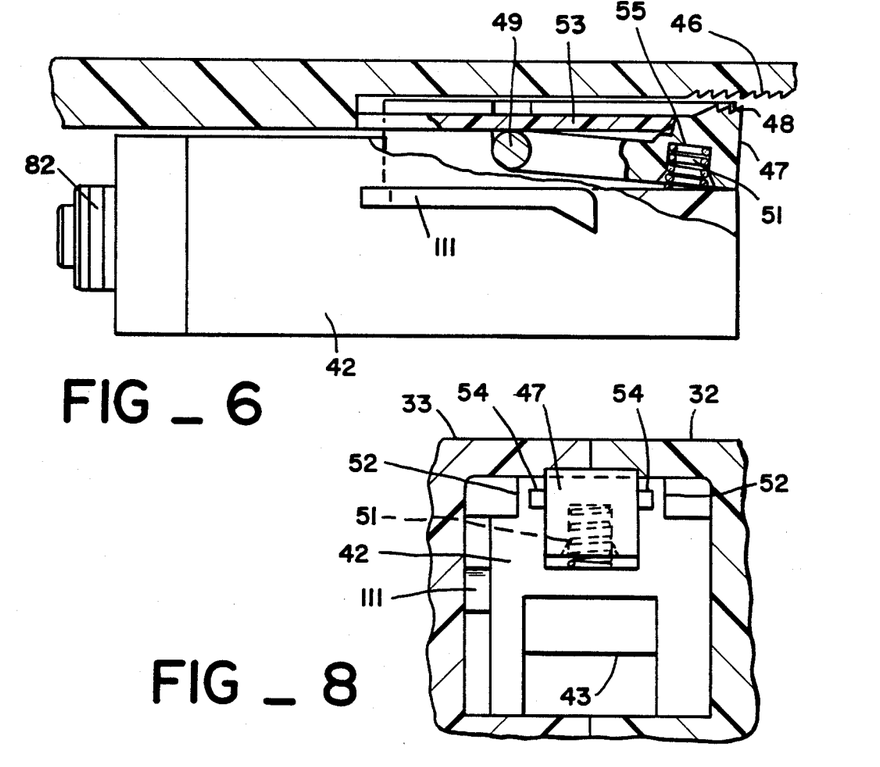
FIG. 6 is an enlarged, partially cross-sectional view of the drive block mechanism of the present invention, shown at its distal limit of translation.
FIG. 8 is an enlarged cross-sectional view of the drive block mechanism, taken along line 8—8 of FIG. 6.
Figures 11, 15, 20:
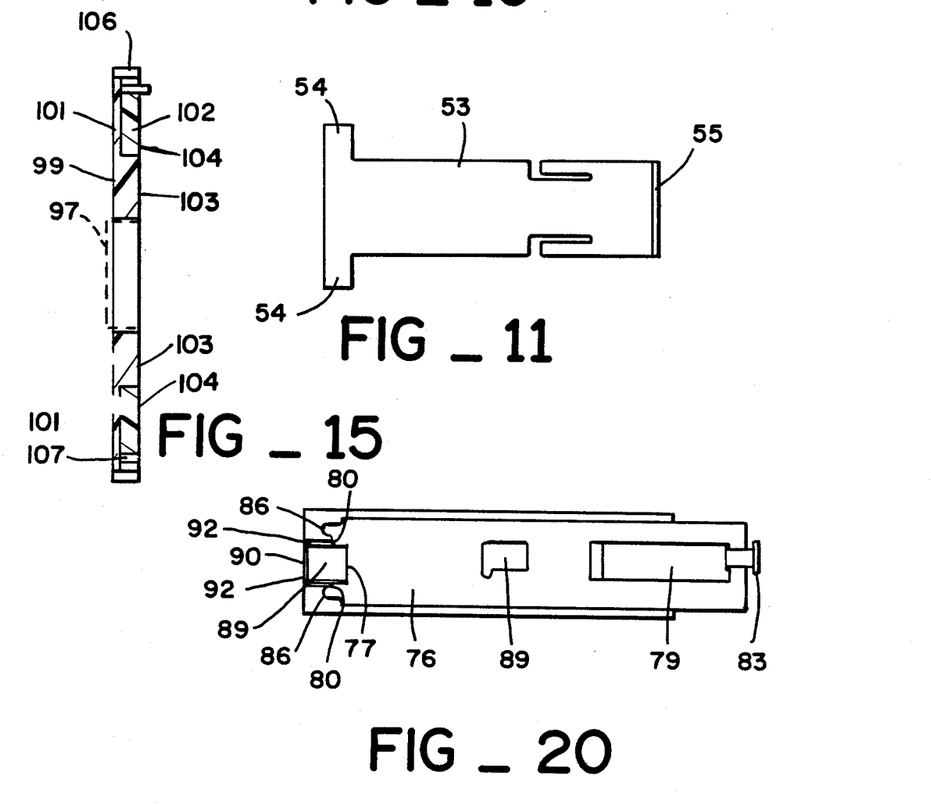
FIG. 11 is a plan view of the stop slide member of the drive block mechanism, as shown in FIGS. 6, 7, and 10.
FIG. 15 is a cross-sectional view of the wheel assembly of the counter assembly, taken along line 15—15 of FIG. 12.
FIG. 20 is a bottom view of the assembled components of the dispensing and crimping mechanism of the tool of the present invention.

A further unique feature of the tool of the present invention, shown in FIGS. 5 and 12-14, comprises a counter to indicate the number of staples remaining in the tool. With reference to FIG. 5, the interior of the housing member 32 is provided with a cylindrical recess 96 located between the trigger pivot pin 37 and the drive track 41, with the display window 29 extending from the recess 96 to the exterior of the tool. A cylindrical pin 97 extends concentrically from the recess 96, and a rectangular extension 98 of the recess extends radially outwardly therefrom. A counter wheel 99 includes an annular groove 101 extending in one face thereof, and a counter wheel 102 is received in the groove 101, as shown in FIG. 15. The wheels 99 and 102 are provided with serial numerical idicia formed on and arrayed about adjacent respective surfaces 103 and 104 thereof. The wheels are received in the recess 96, and wheel 99 includes a central bore dimensioned to receive the pin 97 therethrough. Portions of the indicia on the surfaces 103 and 104 are displayed through the window 29.

Figure 12:
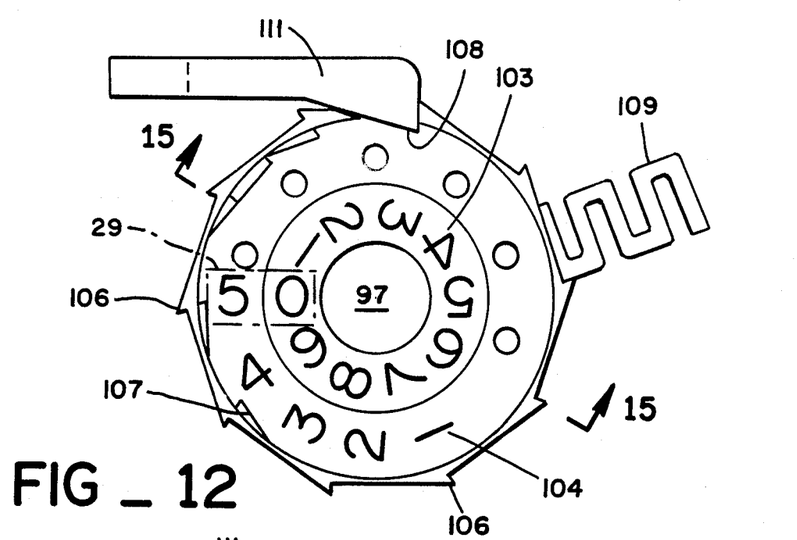
FIGS. 12–14 are a sequence of views depicting the actuation of the counter assembly by the counter pawl of the drive block mechanism.
Figure 13:
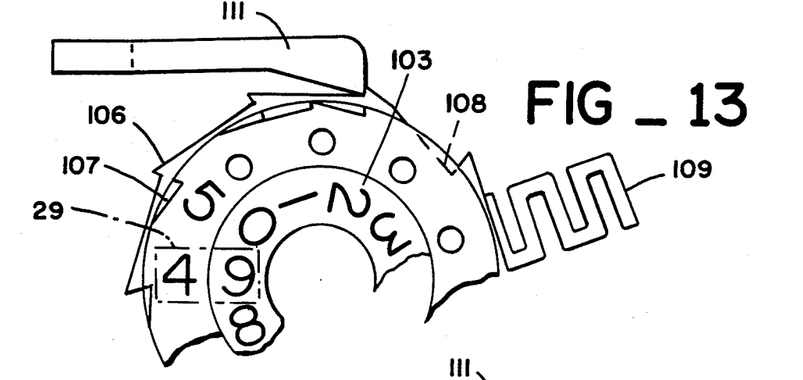
Figure 14:
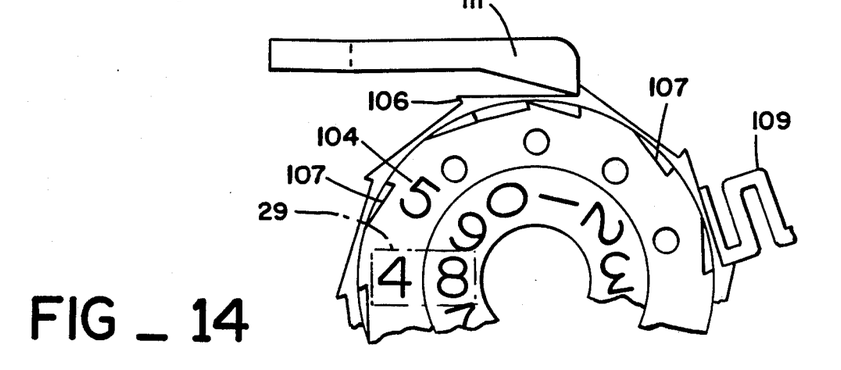

The wheels 99 and 101 are both provided with ten ratchet teet arrayed equally about the peripheral edges thereof. The ratchet teeth 106 of the wheel 99 are closely adjacent to the ratchet teeth 107 of the wheel 102, due to the nested relationship of the wheels. Furthermore, one of the teeth 108 of the array of teeth 106 on wheel 99 is provided with a root portion extending radialy inwardly further than the other teeth 106. It should be noted that the ratchet teeth 106 are spaced slightly radially outwardly of the teeth 107, even though the indicia 103 of wheel 99 are spaced radially inwardly of the indicia 104. As shown in FIGS. 12-14, the indicia 103 comprise numerals one through nine, representing unit numbers, and the indicia 104 comprise numerals one through five, representing tens of units. A stop spring 109 is received in the rectangular recess 99, and arranged to extend to and engage the ratchet teeth 106 to prevent counterclockwise roation thereof, as seen in FIGS. 12-14.

The drive block 42 is provided with a counter pawl 111 extending therefrom and arranged to impinge on the nested counter wheels as the drive block translates proximally to its quiescent position in the drive track 41. The counter wheels are arranged so that the initial impingement of the pawl 111 on the wheels engages the deeper root of ratchet tooth 108, permitting the pawl to also engage one of the teeth 107 of wheel 102. As a result, the first impingement of the pawl on the wheels rotates both counter wheels, decrementing both the tens and units indicia displayed in the window 29, as shown in the transition from FIG. 12 to FIG. 13. Thereafter, the subsequent proximal return of the drive block causes the pawl 111 to engage the next ratchet tooth 106, which is not sufficiently deep to permit engagement of the teeth 107. Thus the wheel 99 is decremented by one unit indicia for each proximal return of the drive block. After ten decrements of the wheel 99, the ratchet tooth 108 has rotated fully about the wheel, and is positioned to be engaged again by the pawl 111. The wheel 104 is thus again decremented by the subsequent drive block return, so that the counter display is decremented serially from the initial setting (fifty, in the preferred embodiment) to zero.

It may be appreciated that the present invention provides a superior tool for storing, dispensing, and applying surgical staples. The mechanism of the tool is extremely simplified, utilizing a minimum of moving parts, so that the tool may be economically produced for disposable after one use. The action of the mechanism is smooth and continuous, and jam-proof. The barrel may be rotated to any angle for dispensing and applying staples without affecting the action of the mechanism whatsoever. And, the dispensing cycle may be interrupted at any point without adversely affecting or jamming the mechanism, so that a staple may be partially dispensed and crimped before it is placed in tissue and subsequently fully crimped.

We claim:

1. A device fo storing, dispensing, and applying a plurality of surgical staples in serial fashion, including a housing, a staple track extending along a first axis for storing a said plurality of staples in parallel, stacked, column fashion, means for urging said staples toward a distal outlet end of said staple track, said staple track including a distal portion curved out of alignment with said first axis so that the staples in said distal track portion are urged into points-first alignment as said staples traverse said distal track portion, a form tool disposed in said housing parallel and adjacent to said staple track, means for translating said form tool reciprocally in a dispensing feed path parallel to said first axis, drag spring means coupled to said form tool and positioned with respect to said distal outlet end of said staple track to capture and move the distal-most staple in said staple track from said outlet end of said staple track to said dispensing feed path as said from tool translates proximally parallel to said first axis, a fixed anvil member disposed at a distal end of said dispensing feed path, said form tool including means for urging said staple in said dispensing feed path distally therealong into impingement with said anvil to crimp said staple thereabout.

2. The device of claim 1, wherein said means for translating said form tool reciprocally parallel to said first axis includes a drive block coupled to said form tool, a drive track formed in said housing and extending generally parallel to said first axis, said drive block secured in said drive track in reciprocally translating fashion, and trigger lever means for engaging said drive block and urging said drive block distally in said drive track.

3. The device of claim 2, further including counter means for displaying the number of staples remaining in said device.

4. The device of claim 3, wherein said counter means includes a display window in said housing, and indicia means disposed in registration with said display window.

5. The device of claim 4, wherein said indicia means includes a first indicia wheel having an annular groove formed in one end face thereof, and a second indicia wheel having an annular portion dimensioned to be received in said annular groove in rotatable fashion.

6. The device of claim 5, wherein said first indicia wheel includes an annular surface spaced radially inwardly from said annular groove on said one end face, said annular surface having serial indicia spaced thereabout indicative of unit decrements, said second indicia wheel having an annular end surface with serial indicia spaced thereabout indicative of tens decrements.

7. The device of claim 5, wherein said first and second indicia wheels include a plurality of ratchet teeth spaced circumferentially thereabout, and further including a counter pawl extending from said drive block and disposed to engage said ratchet teeth and rotate said indicia wheels as said drive block translates proximally in said drive track.

8. The devie of claim 7, wherein said ratchet teeth on said first indicia wheel extend to a greater diameter than said ratchet teeth on said second indicia wheel, whereby said counter pawl generally engages said ratchet teeth of said first indicia wheel, said first indicia wheel further including at least one ratchet tooth having a root portion extending sufficiently radially inwardly therein to permit said counter pawl to engage said ratchet teeth of said second indicia wheeland rotate said first and second indicia wheels together.

9. The device of claim 2, further including first ratchet means engaging said drive block and preventing proximal translation of said drive block as said drive block proceeds distally along said drive track, and means for releasing said first ratchet means as said drive block translates to the distal end of said drive track.

10. The device of claim 9, wherein said housing is formed in a pistol-like configuration having a barrel portion extending generally parallel to said fist axis, and a handle portion extending generally transverse to said barrel portion, said trigger lever means including a trigger retractable in said handle portion.

11. The device of claim 10, wherein said barrel portion is rotatably secured to said handle portion for rotation about said first axis.

12. The device of claim 11, wherein said trigger lever is pivotable about an axis extending generally transverse to said first axis and nonintersecting therewith.

13. The device of claim 9, wherein said first ratchet means includes a plurality of ratchet teeth arrayed in generally linear fashion adjacent to said drive track, and a ratchet pawl arm extending from said drive block to engage said ratchet teeth.

14. The device of claim 13, wherein said means for releasing said first ratchet means includes a release member secured to said drive block and disposed to be actuated as said drive block translates to the distal end of said drive track to retract said ratchet pawl arm from engagement with said ratchet teeth.

15. The device of claim 14, wherein said drive block includes a channel extending therealong generally parallel to said first axis, said release member being slidably received in said channel, said slide member including a distal end adapted to impinge upon the distal end of said drive track and a proixmal end disposed to impinge upon and release said ratchet pawl arm from engagement with said ratchet teeth.

16. The device of claim 2, wherein said drive block includes a plurality of gear teeth in rack formation, and said trigger lever means includes a trigger lever pivotally secured in said housing, said trigger lever including a plurality of pinion teeth engaging said gear teeth in rach-and-pinion fashion to translate said drive block reciprocally along said drive track as said trigger lever is squeezed and released.

17. The device of claim 1, wherein said means for urging said staples toward a distal outlet end of said staple track includes a staple pusher member received in said staple track, and resilient means for exerting a constant force on said staple pusher member and said staples in the distal, axial direction.

18. The device of claim 17, wherein said staple pusher member includes a medial portion having a pusher surface disposed to engage the medial web portion of the proximal-most staple of said parallel, stacked column, and a pair of tab portions disposed on laterally opposed sides of said medial portion and disposed to engage the laterally opposed portions of said proximal-most staple.

19. The device of claim 18, wherein said tab portions include means for permitting flexure of said tab portions as said tab portions traverse and bend in said distal curved portion of said staple track.

20. The device of claim 1, wherein said distal track portion includes a lip extending transversely to said first axis and separating said dispensing feed path from said distal portion of said staple track, said lip being disposed to engage the points of said distal-most staple, said distal-most staple being disposed to impinge upon and prevent the points of said staple in said dispensing feed path from returning past said lip and reentering said distal portion of said staple track.

21. The device of claim 1, wherein said drag spring means includes a drag spring having a pair of fingers extending distally therefrom, said drag spring fingers having like dogleg configurations that define with the distal portion of said form tool a concave recess dimensioned to receive and retain the web portion of said distal-most staple.

22. The device of claim 21, wherein said drag spring fingers are resilient, said drag spring is translatable in a linear direction parallel to said first axis, and further including means for selectively coupling said translation of said form tool to operatively translate said drag spring so that said staple captured and moved to said dispensing feed path is translated proximally with respect to said outlet end of said staple track.

23. The device of claim 1, further including ejection spring means for releasing a crimped staple from engagement with said fixed anvil member.

24. The device of claim 23, wherein said ejection spring means includes a pair of spring arms extending generally parallel to said first axis and disposed at laterally opposed sides of said fixed anvil and within said dispensing feed path, said spring arms being resilient to be deflected by passage of a staple thereby along said dispensing feed path and to exert a resilient restoring force on said staple after crimping thereof about said fixed anvil member.

25. The device of claim 1, further compression spring means secured between said housing and said form tool and disposed to be compressed resiliently by distal translation of said form tool.

26. A device for storing, dispensing, and applying a plurality of surgical staples in serial fashion, including a housing, staple track means for storing said plurality of staples in column fashion, means for advancing one of said staples from said staple track means to a dispensing feed path, a fixed anvil disposed in said dispensing feed path, means for engaging and translating the staple disposed in said dispensing feed path and urging said staple into impingement with said fixed anvil to crimp said staple thereabout, said means for engaging and translating including drive block means operatively coupled thereto in motion transferring, actuating relationship, said drive block means including a drive track extending in said housing, a drive block retained in said drive track in freely translating fashion, trigger lever means pivotally secured in said housing and extendable therefrom for manual actuation, means for operatively coupling said trigger lever means to translate said drive block reciprocally along said drive track distally toward and proximally away from said means for engaging and translating as said trigger lever is squeezed and released with respect to said housing, first ratchet means for preventin proximal translation of said drive block as said drive block is translated distally along said drive track, means for releasing said first ratchet means as said drive block is translated to the distal end of said drive track, said first ratchet means including a plurality of fine pitch ratchet teeth extending in a continuous array in generally linear fashion adjacent to said drive track, and a ratchet pawl arm extending from said drive block to engage said ratchet teeth.

27. The device of claim 26, wherein said means for releasing said first ratchet means includes a release member slidably secured to said drive block and disposed to be actuated as said drive block translates to the distal end of said drive track to slide proximally with respect to said drive block and impinge upon and retract said ratchet pawl arm from engagement with said ratchet teeth.

28. The device of claim 27, wherein said drive block includes a channel extending therealong generally parallel to said first axis, said release member being slidably received in said channel, said slide member including a distal end adapted to impinge upon the distal end of said drive track and a proximal end disposed to impinge upon and release said ratchet pawl arm from engagement with said ratchet teeth.

29. The device of claim 26, wherein said drive block includes a plurality of gear teeth in rack information, and said trigger lever means includes a trigger lever piovtally secured in said housing, said trigger lever including a plurality of pinion teeth engaging said gear teeth in rack-and-pinion fashion to translate said drive block reciprocally along said drive track as said trigger lever is squeezed and released.

30. The device of claim 26, wherein said ratchet pawl arm includes another plurality of fine pitch ratchet teeth extendíng in a continuous array in generally linear fashion and disposed to engage said ratchet teeth of said first ratchet means.

31. A device for storing, dispensing, and applying a plurality of surgical staples in serial fashion, including a housing, staple track means for storing said plurality of staples in column fashion, means for advancing one of said staples from said staple track means to a dispensing feed path, a fixed anvil disposed in said dispensing feed path, means for engaging and translating the staple disposed in said dispensing feed path and urging said staple into impingement with said fixed anvil to crimp said staple thereabout, said means for engaging and translating including drive block means oepratively coupled thereto in translating including drive block means operatively coupled thereto ih motion transferring, actuating relationship, said drive block means including a drive track extending in said housing, a drive block retained in said drive track in freely translating fashion, trigger lever means pivotally secured in said housing and extendable therefrom for manual actuation, means for operatively coupling said trigger lever means to translate said drive block reciprocally along said drive track distally toward and proximally away from said means for engaging and translating as said trigger lever is squeezed and released with respect to said housing, counter means for displaying the number of staples remaining in said device, said counter means including a display window in said housing, indicia means disposed in registration with said display window, said indicia means including a first indicia wheel having an annular groove formed in one end face thereof, and a second indicia wheel having an annular portion dimensioned to be received in said annular groove in rotatable fashion.

32. The device of claim 31, wherein said first indicia wheel includes an annular surface spaced raially inwardly from said annular groove on said one end face, said annular surface having serial indicia spaced thereabout indicative of unit decrements, said second indicia wheel having an annular end surface with serial indicia spaced thereabout indicative of ten decrements.

33. The device of claim 31, wherein said first and seocnd indicia wheels include a plurality of ratchet teeth spaced circumferentially thereabout, and further including a counter pawl extending from said drive block and disposed to engage said ratchet teeth and rotate said indicia wheels as said drive block translates proximally in said drive track.

34. The device of claim 33, wherein said ratchet teeth on said first indicia wheel extend to a greater diameter than said ratchet teeth on said second indicia wheel, whereby said counter pawl generally engages said ratchet teeth of said first indicia wheel, said first indicia wheel further including at least one ratchet tooth having a root portion extending sufficiently radially inwardly therein to permit said counter pawl to engage said ratchet teeth of said second indicia wheel and rotate said first and second indicia wheels together.

* * * * *